(12) United States Patent
Roby et al.

(10) Patent No.: US 6,494,898 B1
(45) Date of Patent: Dec. 17, 2002

(54) ABSORBABLE COPOLYMERS AND SURGICAL ARTICLES FABRICATED THEREFROM

(75) Inventors: Mark S. Roby, Killingworth, CT (US); Ying Jiang, Raleigh, NC (US); Lyudmila K. Kokish, Orange, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/161,606

(22) Filed: Sep. 26, 1998

Related U.S. Application Data

(63) Continuation-in-part of application No. 09/030,191, filed on Feb. 25, 1998, now abandoned.

(51) Int. Cl.$^7$ ............................................. A61B 17/04

(52) U.S. Cl. .................. 606/230; 606/231; 525/411; 525/413; 528/354

(58) Field of Search ................................ 606/230, 231

(56) References Cited

U.S. PATENT DOCUMENTS

| | | | |
|---|---|---|---|
| 4,045,418 A | 8/1977 | Sinclair | 260/78.3 |
| 4,052,988 A | 10/1977 | Doddi et al. | |
| 4,057,537 A | 11/1977 | Sinclair | 260/78.3 R |
| 4,605,730 A | 8/1986 | Shalaby et al. | 528/357 |
| 4,643,191 A | 2/1987 | Bezwada et al. | |
| 4,653,497 A | 3/1987 | Bezwada et al. | |
| 4,700,704 A | 10/1987 | Jamiolkowki et al. | |
| 4,838,267 A | 6/1989 | Jamiolkowki et al. | |
| 4,994,074 A | 2/1991 | Bezwada et al. | 606/230 |
| 5,047,048 A | 9/1991 | Bezwada et al. | 606/231 |
| 5,076,807 A | 12/1991 | Bezwada et al. | 606/230 |
| 5,133,739 A | 7/1992 | Bezwada et al. | 606/230 |
| 5,468,253 A | 11/1995 | Bezwada et al. | 606/230 |
| 5,554,170 A * | 9/1996 | Roby et al. | 606/230 |
| 5,713,920 A | 2/1998 | Bezwada et al. | 606/230 |

* cited by examiner

*Primary Examiner*—Gary Jackson

(57) ABSTRACT

A synthetic absorbable monofilament comprising glycolide and epsilon caprolactone is provided. The monofilament exhibits physical characteristics equivalent to or superior than gut sutures. The monofilaments can be fabricated into a wide variety of surgical devices such as sutures, meshes, and the like.

12 Claims, 2 Drawing Sheets

ABSORBABLE COPOLYMERS AND SURGICAL ARTICLES FABRICATED THEREFROM

This application is a continuation-in-part of Ser. No. 09/030,191 filed Feb. 25, 1998 now abandoned.

TECHNICAL FIELD

Absorbable copolymers of randomly polymerized glycolide and caprolactone are described. Processes for making the copolymers and surgical articles made totally or in part from such copolymers, including sutures, are also described.

BACKGROUND

Bioabsorbable surgical devices made from copolymers derived from glycolide and epsilon-caprolactone are known in the art. Such bioabsorbable surgical devices include surgical sutures.

A desirable characteristic of a bioabsorbable suture is its ability to exhibit and maintain desired tensile properties for a predetermined time period followed by rapid absorption of the suture mass (hereinafter "mass loss".)

Synthetic absorbable sutures are known in the art. Absorbable multifilament sutures such as DEXON sutures (made from glycolide homopolymer and commercially available from Davis & Geck, Danbury, Conn.), VICRYL sutures (made from a copolymer of glycolide and lactide and commercially available from Ethicon, Inc., Sommerville, N.J.), and POLYSORB sutures (also made from a copolymer of glycolide and lactide and commercially available from United States Surgical Corporation, Norwalk, Conn.) are known in the industry as short term absorbable sutures. The classification short term absorbable sutures generally refers to surgical sutures which retain at least about 20 percent of their original strength at three weeks after implantation, with the suture mass being essentially absorbed in the body within about 60 to 90 days post implantation.

Long term absorbable sutures are generally classified as sutures capable of retaining at least about 20 percent of their original strength for six or more weeks after implantation, with the suture mass being essentially absorbed in the body within about 180 days post implantation. For example, PDS II sutures (commercially available from Ethicon, Inc., Sommerville, N.J.), are synthetic absorbable monofilament sutures that reportedly retain at least about 20 to 30 percent of its original strength six weeks after implantation. However, PDS II reportedly exhibits minimal mass loss until 90 days after implantation with the suture mass being essentially absorbed in the body about 180 days after implantation. MAXON suture (commercially available from Davis & Geck, Danbury, Conn.) is another absorbable synthetic monofilament that reportedly generally fits this absorption profile.

Most recently, United States Surgical Corporation has introduced BIOSYN monofilament sutures which exhibit good flexibility, handling characteristics, knot strength and absorption characteristics similar to those of presently available short term absorbable multifilament sutures.

Another attempt to provide an acceptable synthetic absorbable monofilament sutures resulted in MONOCRYL, a suture fabricated from an absorbable block copolymer containg glycolide and caprolactone, commercially available from Ethicon, Inc.

However, no synthetic absorbable monofilament sutures exist today which approximate the strength retention, mass loss, and modulus of sutures commonly referred to in the art as "catgut" or "gut" sutures. It is well known in the art that the term gut suture refers to a collagen based suture of any type or origin often fabricated from the mammalian intestines, such as the serosal layer of bovine intestines or the submucosal fibrous layer of layer sheep intestines. Gut sutures exhibit the unique combination of two week strength retention and about 75 day mass loss while maintaining acceptable modulus and tensile strength; and thus are still widely used in gynecological surgery.

It would be advantageous to provide a synthetic absorbable suture which exhibits physical properties similar to the gut suture.

U.S. Pat. No. 4,700,704 to Jamiolkowski does teach that sutures can be fabricated from random copolymers of glycolide and epsilon-caprolactone, and more specifically from random copolymers containing from 20 to 35 weight percent epsilon-caprolactone and from 65 to 80 weight percent glycolide. Moreover, Jamiolkowski reports that sutures fabricated from glycolide/epsilon-caprolactone copolymers containing over 35% caprolactone under are not orientable to a dimensionally stable fiber. Jamiolkowski further reports that some sutures fabricated from glycolide/epsilon-caprolactone copolymers containing 15% caprolactone are also not orientable to a dimensionally stable fiber. Furhermore, Jamiolkowski also reports the undesirable combination of low modulus and low tensile strength for the glycolide/epsilon-caprolactone copolymers which he was able to fabricate into sutures.

Therefore, it would be unexpected that sutures made from random copolymer of glycolide and epsilon-caprolactone would provide the strength retention and mass loss characteristics approximating those of gut sutures while maintaining an acceptable modulus and tensile strength.

SUMMARY

It has now surprisingly been found that absorbable surgical articles formed from a random copolymer of glycolide and caprolactone exhibit strength retention, mass loss and modulus similar to that of gut sutures. Preferably, the copolymers used in forming surgical articles include between about 25 and about 32 weight percent of hydroxy caproic acid ester units and between about 75 and 68 weight percent of glycolic acid ester units.

In particularly useful embodiments, the random copolymers can be spun into fibers. The fibers can be advantageously fabricated into either monofilament or multifilament sutures having physical properties similar to those of gut sutures.

In addition, a process of making such synthetic absorbable monofilament sutures from the above described caprolactone/glycolide random copolymers has been found. The process, for a given size suture, comprises the operations of extruding the random caprolactone/glycolide copolymer at an extrusion temperature of from about 70° C. to about 215° C. to provide a monofilament fiber, passing the solidified monofilament through water (or other suitable liquid medium) quench bath at a temperature of from about 15° C. to about 25° C. or through in air (or other suitable gaseous medium) at from about 15° C. to about 25° C., stretching the monofilament through a series air ovens at an overall stretch ratio of from about 7:1 to about 14:1 to provide a stretched monofilament. In a particularly useful embodiment, the monofilament is stretched through three air ovens by four godet stations. The first air oven is maintained at ambient temperature, whereas the second air oven is heated to a temperature above the crystalization temperature of the glycolide/epsilon caprolactone copolymer at about 80° C. to about 110° C., and the third air oven is set at about 85° C. to about 120° C. The draw ratio between the first and second godet station ranges between about 5:1 to about 8:1. The draw ratio between the second and third godet station ranges between about 1.3:1 to about 1.8:1. The draw ratio between the third and fourth godet station ranges between about 1.04:1 to about 1.06:1. The suture then may be annealed with or without relaxation at a temperature of from about 80° C. to about 120° C. to provide the finished suture.

DESCRIPTION OF THE PREFERRED EMBODIMENTS

It has been found that glycolide and epsiloncaprolactone monomers can advantageously be combined to form a random copolymer useful in forming surgical articles having strength retention, mass loss, and modulus characteristics similar to or superior to gut sutures.

The random copolymer can be prepared using conventional techniques. For example, monomers can be dried, mixed in a reaction vessel with an initiator (either a single or multifunctional initiator) and a suitable polymerization catalyst and heated at temperatures from about 170° C. to about 200° C. for a period of time ranging from about 10 hours to about 30 hours.

The copolymer has repeating units derived from glycolide randomly combined with repeating units derived from caprolactone. Repeating units derived from glycolide comprise between about 25 and about 32 weight percent of the copolymer and preferably about 30 weight percent of caprolactone and about 70 weight percent of gylcolide. Copolymers of caprolactone and glycolide having an inherent viscosity of from about 1.0 to about 1.8 dl/g measured at 30° C. and at a concentration of 0.25 g/dl in chloroform or HFIP may generally be used.

The random copolymers can be formed into surgical articles using any known technique, such as, for example, extrusion, molding and/or solvent casting. The copolymers can be used alone, blended with other absorbable compositions, or in combination with non-absorbable components. A wide variety of surgical articles can be manufactured from the copolymers described herein. These include but are not limited to clips and other fasteners, staples, sutures, pins, screws, prosthetic devices, wound dressings, drug delivery devices, anastomosis rings, and other implantable devices. Fibers made from the copolymers can be knitted, woven or made into non-woven materials with other fibers, either absorbable or nonabsorbable to form fabrics, such as meshes and felts. Compositions including these random copolymers can also be used as an absorbable coating for surgical devices. Preferably, however, the copolymers are spun into fibers to be used in making sutures.

Multifilament sutures of the present invention may be made by methods known in the art. Braid constructions such as those disclosed and claimed in U.S. Pat. Nos. 5,059,213 and 5,019,093 are suitable for the multifilament suture of the present invention.

Figure 1:
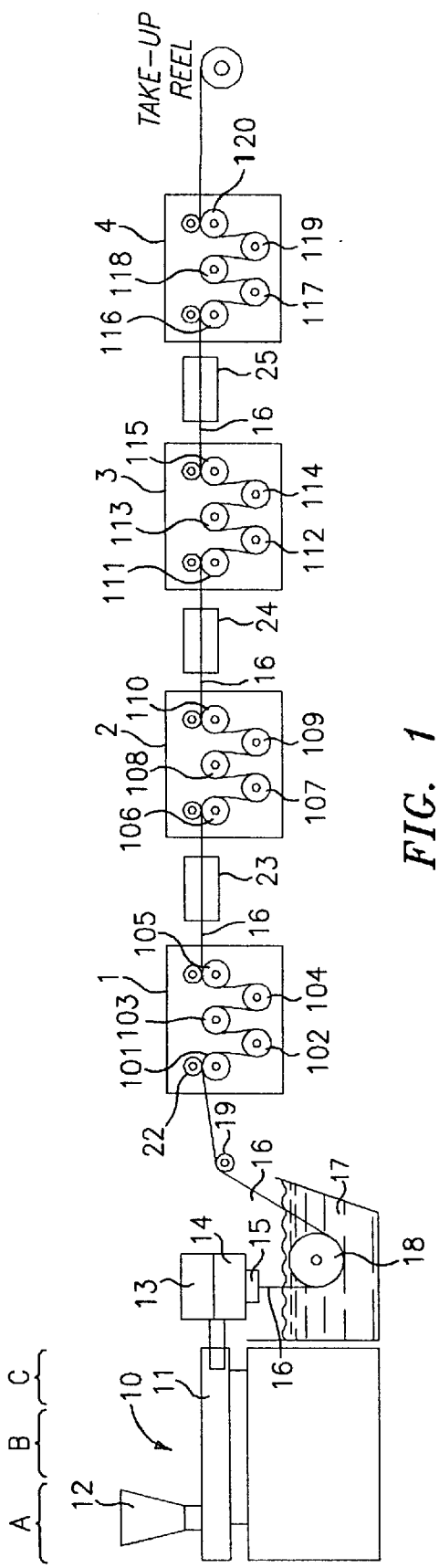
FIG. 1 is a schematic illustration of an apparatus which is suitable for manufacturing of monofilament sutures disclosed herein.

FIG. 1 substantially illustrates the extruding, quenching and stretching operations of the monofilament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the above described copolymers which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 170° C. to 215° C., zone B at from about 170° C. to 215° C. and zone C at from about 170° C. to about 215° C. Additional temperature parameters include: metering pump block 13 at from about 170° C. to about 215° C., spinneret 15 at from about 170° C. to about 225° C. and quench bath at from about 15° C. to about 40° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is passed through first godet station 1, which is equiped with five individual godets, i.e. godets 101, 102, 103, 104 and 105. Upon entering godet station 1, monofilament 16 is wrapped around a first godet 101 provided with nip roll 22 to prevent slippage which might otherwise result from the subsequent stretching operation; and subsequently passed over godet 101, under godet 102, over godet 103, under godet 104, and over godet 105 to godet station 2, containing godets 106, 107, 108, 109, and 110, where it is wrapped over godet 106, under godet 107, over godet 108, under godet 109, and over godet 110. Monofilament 16 passing from godet station 1 to godet station 2 is drawn through air oven 23 at a temperature ranging form about 20° C. to about 30° C. by the godets of godet station 2 which rotate at speeds faster than the speed of the godet station 1 to provide the desired draw ratio, which is from about 5:1 to about 10:1 and preferably from about 6:1 to about 8:1, to effect the molecular orientation of the copolymer from which it is fabricated and thereby increase its tensile strength.

Following the initial draw at ambient temperature, monofilament 16 is then subjected to a second and a third drawing operation. Monofilament 16 is subsequently drawn from godet 105 through air oven 24, which is maintained at from about 80° C. to about 110° C., to godet station 3 containing godets 111, 112, 113, 114, and 115 where it is wrapped over godet 111, under godet 112, over godet 113, under godet 114, and over godet 115. Godet station 3 spins faster than godet station 2 to provide the desired draw ratio, which is from about 1.3:1 to about 1.8:1. Monofilament 16 is then drawn from godet 115 through air oven 25, which is maintained at from about 85° C. to about 120° C., by godet station 4, containing godets 116, 117 118, 119, and 120 where it is wrapped over godet 116, under godet 117, over godet 118, under godet 119, and over godet 120. Godet station 4 spins faster than godet station 3 to provide the desired draw ratio, which is from about 1.05:1 to about 1.06:1. It should be understood that the godet arrangements in each of godet stations 1, 2, 3, and 4, respectively should not be limited to the above described arrangement and that each godet station may have any suitable godet arrangement.

In an alternative operation for sutures for smaller size sutures, sizes 4/0 to 8/0, monofilament 16 is only passed through godet stations 1 and 2 and not subjected to any further stetching operations.

Annealing of the suture also may be accomplished with or without shrinkage of the suture. In carrying out the annealing operation, the desired length of suture may be wound around a creel and the creel placed in a heating cabinet under nitrogen flow maintained at the desired temperature, e.g. about 70° C. to about 120° C., as described in U.S. Pat. No. 3,630,205. After a suitable period of residency in the heating cabinet, e.g., for up to about 18 hours or so, the suture will have undergone essentially no shrinkage. As shown in U.S. Pat. No. 3,630,205, the creel may be rotated within the heating cabinet to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Alternatively, the suture may be annealed on line with or without relaxation. For relaxation, the fourth godet station rotates at a slower speed than the third godet station thus relieving tension on the filament.

Figure 2:
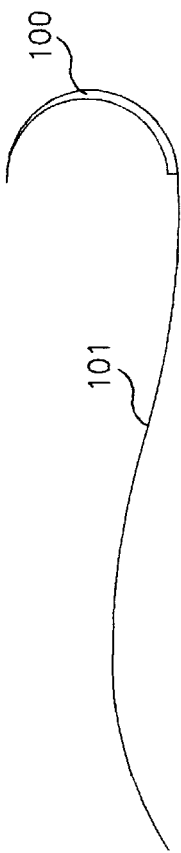
FIG. 2 is a perspective view of a suture attached to a needle.

The suture disclosed herein, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present invention in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

In order that those skilled in the art may be better able to practice the compositions and methods described herein, the following example is given as an illustration of the preparation of random copolymers as well as of the preparation and superior characteristics of sutures made from the random copolymers. It should be noted that the invention is not limited to the specific details embodied in the examples and further that all ratios or parts recited are by weight, unless otherwise indicated.

EXAMPLE 1

Dry glycolide (4200 grams) and undistilled epsilon-caprolactone were added to a reactor along with 0.35 grams of distilled stannous octoate and 3 grams of 1,6 hexanediol. The mixture was dried for about 48 hours with agitation under flow of nitrogen. The reactor temperature was then set at 100° C. When the temperature of the reactants reached 100° C. the temperature was maintained for about 15 minutes at which point the temperature of the reactants was raised to about 150° C. and the reaction vessel heated for about an additional 15 minutes. The temperature of the reactants was then raised to about 190° C. and polymerization conducted with stirring under a nitrogen atmosphere for about 18 hours. The reaction product is then isolated, comminuted, and treated to remove residual reactants using known techniques. The treatment to remove residual reactants occurs at 130° C. for 48 hours under vaccuum.

Table I below sets forth typical conditions for extruding, stretching of size 3/0 sutures in accordance with this invention. All of the monofilament sutures were fabricated from the resin of Example 1.

TABLE I

CONDITIONS OF MANUFACTURING VARIOUS SIZES OF MONOFILAMENT OF THE PRESENT INVENTION

| Example | 1 |
|---|---|
| Suture Size | 3/0 |
| Process Conditions | Extrusion |
| extruder screw, rpm | 7 |
| pump, rpm | 15.4 |
| driven roller, mpm | 2.7 |
| barrel temp., ° C., zone A | 183 |
| barrel temp., ° C., zone B | 186 |
| barrel temp., ° C., zone C | 189 |
| clamp temp., ° C. | 188 |
| adapter temp., ° C. | 189 |
| pump temp., ° C. | 196 |
| block temp., ° C. | 190 |
| barrel melt temp., ° C. | 192 |

TABLE I-continued

CONDITIONS OF MANUFACTURING VARIOUS SIZES
OF MONOFILAMENT OF THE PRESENT INVENTION

| | |
|---|---|
| pump melt temp., ° C. | 191 |
| spinneret melt temp., ° C. | 194 |
| barrel pressure, psi | 1040 |
| pump pressure, psi | 1000 |
| spinneret pressure, psi | 1400 |
| pump size, cc per revolution | 0.16 |
| diameter of spinneret, orifices, mm | 1.2 |
| no. of spinneret orifices | 1 |
| quench bath temp., ° C. | 20 |
| Stretching (Orienting) Operation | |
| Example | |
| draw bath temp., ° C. | ambient |
| first godet station, mpm | 2.9 |
| second godet, mpm | 20.8 |
| third godet station, mpm | 34.6 |
| fourth godet station, mpm | 36.2 |
| first oven temp, ° C. | 25 |
| second oven temp, ° C. | 85 |
| third oven temp, ° C. | 90 |
| overall draw ratio | 12.57:1 |
| Annealing Operation | |
| Example | 1 |
| annealing temp., ° C. | 80°C. |
| time (hrs.) | 6 |

The physical properties of the sutures and the procedures employed for their measurement are set forth in Table II as follows:

TABLE II

PROCEDURES FOR MEASURING PHYSICAL PROPERTIES
OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |
| Young's Modulus | Instron Merlin Software version 2000 Series IX calculation 18.3 (commercially available from Instron Corporation) |

Table III below sets forth the physical properties of the size 3/0 suture of the present invention.

TABLE III

| Physical Property | Example 1 |
|---|---|
| diameter (mm) | .298 |
| knot-pull strength (kg) | 2.66 |
| Young's Modulus (kpsi) | 170 |
| Elongation % | 22 |
| Tensile Strength (kpsi) | 102.2 |

As the data in Tables III illustrates, the suture made of the copolymer provided herein shows a desired physical properties, such as modulus and tensile strength.

EXAMPLE 2

Invitro Strength Retention

Figure 3A:
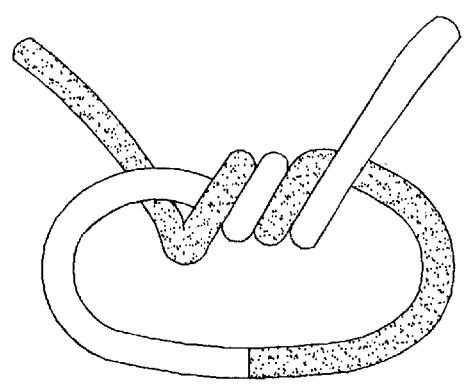
FIGS. 3A–3C illustrate the formation of the knot which was employed in in the loop pull test used in Example 2.
Figure 3B:
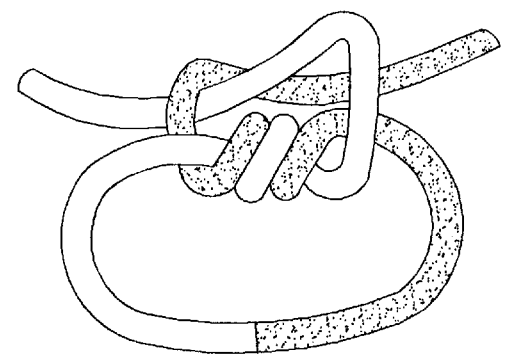
Figure 3C:
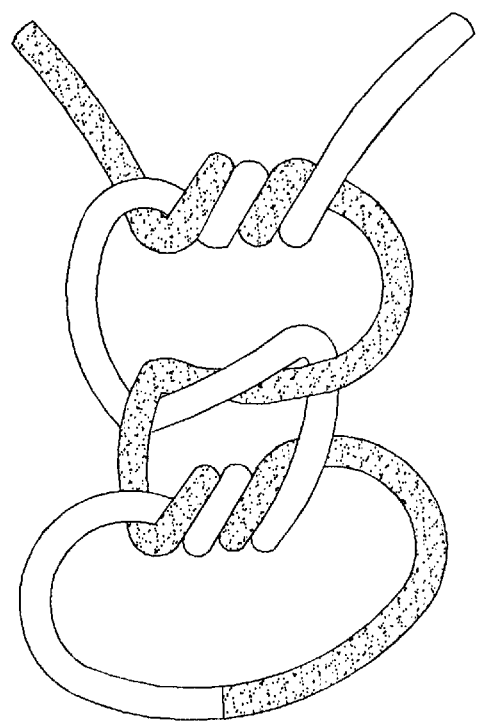

Monofilament sutures manufactured in accordance with the above described process using the copolymer of Example 1 were tested for in vitro strength retention. In vitro loop-pull strength retention is indicative of in vivo strength retention. The in vitro strength retention of the suture was tested as follows:

To simulate in vivo conditions, the suture samples were stored in a container filled with Sorenson's buffer solution at 37° C. After various periods of time, the suture samples were then removed from the container to test their loop-pull strength as follows. A knotted loop was formed in a test suture in three steps as shown in FIGS. 3A–3C. As shown in step 1 of of FIG. 3A, each suture was given a double throw (left over right) around a 2 cm diameter cylinder. In Step 2, the free ends of the suture were set in a single throw throw (right over left) onto the initial throw of step 1. Finally, in step 3, another double throw (left over right) was set onto the single throw of Step 2 to complete the knot. The free ends of the suture were cut to approximately 0.5 inches and the loop was carefully eased from the cylinder.

Testing of the loop was carried out useing an Instron Corporation (Canton, Mass.) Tensile Tester Model No. 4307, operated with a crosshead speed of 51 mm/min and equipped with flat grips, each having a pin over which the loop is positioned.

The results of the tests are presented in Table IV hereinbelow. In the strength retention data reported in Table II, $T_n$ represents the time elapsed in weeks since the sample was placed in the solution, with n representing the number of weeks.

TABLE IV

PERCENTAGE OF IN VITRO STRENGTH RETAINED COMPOSITION

| | $T_1$ | $T_2$ | $T_3$ | $T_4$ | $T_6$ | $T_8$ | $T_{10}$ | $T_{12}$ |
|---|---|---|---|---|---|---|---|---|
| EXAMPLE I | 44 | 11 | 0 | — | — | — | — | — |

EXAMPLE 3

In Vitro Mass Loss

Monofilament sutures manufactured in accordance with the above described process using the copolymer of Example 1 were tested for in vitro mass retention. In vitro mass retention strength is indicative of in vivo mass retention. The in vitro strength retention of the suture was tested as follows:

To simulate in vivo conditions, the suture samples were stored in a container filled with Sorenson's buffer solution at 80° C. After various periods of time, the suture samples were then removed from the container filterred, rinsed with distiioled water and dried for about 6 hours at about 40° C. under vaccum and subsequently weighed.

The results of the tests are presented in Table V hereinbelow. In the strength retention data reported in Table V, $T_n$ represents the time elapsed in hours since the sample was placed in the solution, with n representing the number of hours. It is well known in the art that one hour of immersion in the the container filled with Sorenson's buffer solution at 80° C. approximates about one week of invivo mass loss. For comparison purposes, the same tests were conducted on Monocryl sutures.

All comparative tests were performed on size 3/0 sutures.

TABLE V

PERCENTAGE OF IN VITRO MASS RETAINED COMPOSITION

|  | $T_1$ | $T_2$ | $T_3$ | $T_4$ | $T_6$ | $T_8$ | $T_{10}$ | $T_{12}$ |
|---|---|---|---|---|---|---|---|---|
| EXAMPLE I | 92.79 | 66.35 | 51 | 37.73 | 34.31 | 29.35 | 26.97 | 23.58 |
| Monocryl | 94.86 | 74.79 | 66.83 | 47.95 | 42.63 | 35.31 | 32.14 | 27.32 |

Modifications and variations of the compositions and processes disclosed herein are possible in light of the above teachings. It is therefore to be understood that changes may be made in particular embodiments described which are within the full intended scope of the invention as defined by the claims.

What is claimed is:

1. A suture fabricated from a random copolymer comprising from about 68 to about 75 weight percent glycolide and about 25 to about 32 weight percent epsilon-caprolactone, the suture exhibiting two week strength retention, mass loss of about 50% in 32 hours as measured in Sorenson's buffer solution at 80° C. and a modulus ranging from about 150 kpsi to about 250 kpsi and an knot pull strength of about 1.7 to about 2.8 kg.

2. The suture of claim 1 wherein the suture wherein the random copolymer comprises about 30 weight percent glycolide and about 70 weight percent glycolide.

3. The suture of claim 1 wherein the suture is a size 3/0 suture and the modulus is about 170 kpsi.

4. The suture of claim 1 wherein the suture is a size 3/0 suture and the knot pull strength is about 2.6 kg.

5. The suture of claim 1 wherein the suture is a size 3/0 suture and the tensile strength is about 102 kpsi.

6. The suture of claim 1 wherein the suture is a size 3/0 suture and exhibits the following characteristics:

| modulus | about 170 kpsi |
|---|---|
| knot pull strength | about 2.6 kg |
| tensile strength | about 102 kpsi. |

7. The suture of claim 1 comprising a medico-surgically useful substance.

8. The suture of claim 1 wherein the random copolymer possesses an inherent viscosity of about 1.0 to about 1.8 dl/g at 30° C. and a concentration of 0.25 g/dl in HFIP.

9. The suture of claim 1 wherein the suture is a size 3/0 suture and exhibits a mass loss of about 50% after 32 hours in Sorenson's buffer solution at 80° C.

10. The suture of claim 1 wherein the suture is a size 3/0 suture and exhibits a mass loss of about 30% after 72 hours in Sorenson's buffer solution at 80° C.

11. The suture of claim 1 wherein the suture is a size 3/0 suture and exhibits a mass loss of about 12% after 120 hours in Sorenson's buffer solution at 80° C.

12. A method of suturing a wound comprising:

a. providing a suture fabricated from a random copolymer about 68 to about 75 weight percent glycolido and about 25 to about 32 weight percent epsilon-caprolactone, the suture exhibiting two week strength retention, mass loss of about 50% in 32 hours as measured in Sorenson's buffer solution at and a modulus ranging from about 150 to about 250 and an knot pull strength of about 1.7 to about 2.88; and b. passing said needled suture through tissue to create wound closure.

* * * * *